United States Patent [19]

Jacquet et al.

[11] 4,314,808
[45] Feb. 9, 1982

[54] DYE POLYMERS, THEIR PREPARATION AND THEIR USE IN DYE COMPOSITIONS

[75] Inventors: Bernard Jacquet, Antony; Gérard Lang, Epinay-sur-Seine; Serge Forestier, Claye Souilly, all of France

[73] Assignee: L'Oreal, Paris, France

[21] Appl. No.: 151,620

[22] Filed: May 20, 1980

[30] Foreign Application Priority Data

May 25, 1979 [FR] France ................. 79 13347

[51] Int. Cl.³ .................. C09B 1/28; C09B 69/10
[52] U.S. Cl. .......................... 8/405; 8/406;
8/407; 8/647
[58] Field of Search ............ 8/405, 406, 407, 647

[56] References Cited

U.S. PATENT DOCUMENTS 4,228,259 10/1980 Kalopissis et al. ................. 525/435

FOREIGN PATENT DOCUMENTS 861609 3/1978 Belgium .
7009874 1/1971 Netherlands .
2005705 4/1979 United Kingdom .

OTHER PUBLICATIONS

Venkataraman, K., "The Chemistry of Synthetic Dyes," vol. V, (Academic Press, 1971), pp. 532–534.

Primary Examiner—A. Lionel Clingman
Attorney, Agent, or Firm—Cushman, Darby & Cushman

[57] ABSTRACT

A dye polymer for use in dye compositions for coloring keratinic fibers comprises units of the formula

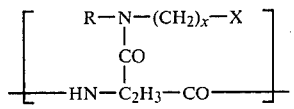

wherein, R represents hydrogen or alkyl, x is a whole number equal at least to 2, and X represents the residue of a molecule of a dye or a dye precursor.

21 Claims, No Drawings

DYE POLYMERS, THEIR PREPARATION AND THEIR USE IN DYE COMPOSITIONS

The present invention relates to a new dye product in the form of a polymer, to a method for preparing the same, and to its use in a dye composition.

It is known that the dyeing of fibers, and, in particular, the dyeing of keratinic fibers, is conventionally carried out using dyes which tend to penetrate the interior of the fiber.

For dyes to be used effectively, they must have a certain affinity for the fiber. However, it has been observed that dyes used for coloring keratinic fibers also have an affinity for the skin. This is disadvantageous not only for the person whose hair is being dyed, but also for the person who applies the dye since the hands of the latter are often stained or colored by the dye. In the case of the person whose hair is being dyed, it has been observed that this person's scalp is also stained or dyed. Moreover, it has been observed that the dye can penetrate the skin and, accordingly, increase the risk of an accident due to its toxicity or cause allergic reactions which are experienced by those having contact with the dye molecule.

The present invention relates to new dye products which avoid to a large extent these disadvantages.

The present invention thus relates to a new dye product comprising at least one polymer containing units of the formula:

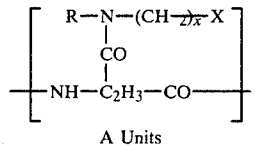

A Units wherein
R represents hydrogen or alkyl,
x is a whole number equal, at least, to 2, and
X represents the residue of a dye molecule or dye precursor.

The invention also relates to a mixture of said polymers.

The polymer of the present invention, also called hereafter a "dye polymer", can be a homopolymer. More generally, it is a copolymer either by reason of the presence of several different A units in the same polymer molecule, or by reason of the presence of units other than the A units in the polymer chain, or also because of the presence, not only of several different A units, but also the presence of units other than A units.

The polymer of the present invention is then, in particular, a polymer containing n types of A units. Such a polymer comprises one having the following units:

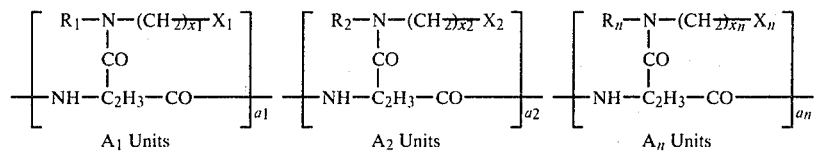

wherein:
$R_1, R_2, \ldots, R_n$, each independently, have the same definition as R, given above;
$x_1, x_2, \ldots, x_n$, each independently, have the same meaning as x, given above;
$a_1, a_2, \ldots, a_n$ are whole numbers, and
$X_1, X_2, \ldots, X_n$, each independently, have the same definition as X, given above. It is to be understood that in this polymer the units $A_1, A_2, \ldots A_n$ are different units.

Generally, n, that is to say, the number of different A units in the same polymer molecule is a number equal, at most, to 10. Preferably, n ranges from 1 to 3. In a given polymer, n has a statistical value ranging preferably from 1 to 3. It is also to be understood that the copolymers of the present invention are obtained in the form of mixtures.

The present invention relates, in particular, to a dye product comprising a polymer of formula (I) containing the following units:

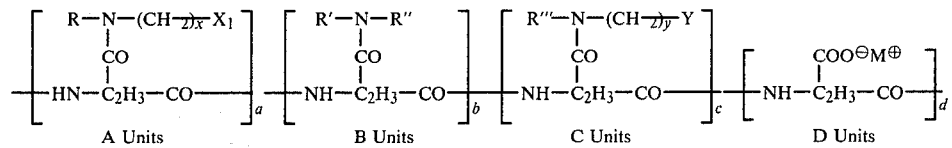

wherein:
R, x and X have the meanings given above,
R' represents hydrogen, lower hydroxy alkyl, alkyl containing 1-18 carbon atoms or alkenyl containing 2 to 18 carbon atoms;
R" represents hydrogen, lower hydroxyalkyl or lower alkyl, or R' and R" together represent with the nitrogen atom to which they are attached a 5 or 6 chain ring, said ring optionally containing another heteroatom selected from oxygen or nitrogen;
y represents a whole number ranging from 2 to 6;
Y represents

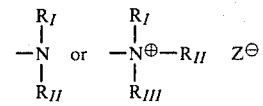

wherein $R_I$, $R_{II}$ and $R_{III}$, each independently, represent hydrogen or an alkyl or alkenyl group having up to 18 carbon atoms, or $R_I$ and $R_{II}$ together with the nitrogen atom to which they are attached form a 5 or 6 chain ring, said ring optionally containing another heteroatom selected from nitrogen or oxygen;
$Z^\ominus$ is an anion;
R''' represents hydrogen or lower alkyl;

M represents hydrogen, an alkali metal atom or a half atom of an alkaline earth metal, or M represents an ammonium ion derived from an amine having one of the following formulas: R—NH—$(CH_2)_{\overline{x}}$X (Amine II), R'—NH—R" (Amine III) or R'''-NH-$(CH_2)_{\overline{y}}$Y (Amine IV), wherein R, x, X, R', R", R''', y and Y have the meanings given above;

a is a whole number excluding zero;

b, c and d are whole numbers, including zero, and such that the sum (a+b+c+d) ranges from 15 to about 500.

The terminal group of the polymer of the present invention can be hydrogen or it can be either a terminal group resulting from the reaction of a terminal group of polydehydroaspartic acid with an amine II, III or IV, as defined above, or a —O⊖M⊕ group, wherein M is defined above.

In units A, B, C or D, the —$C_2H_3$— group can be either $$-\overset{|}{C}H-CH_2-\text{ or }-\overset{CH_2-}{\underset{|}{C}H}-.$$

Thus, for example, units A can be units of the formula,

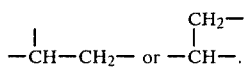

or units of the formula:

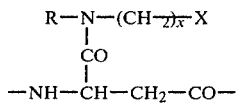

These two types of A units can be present in a given polymer. The same is true for units B, C and D.

It will thus be observed that in a given polymer, the A units can be either all the same, or different, the A units thus corresponding to the n types of different units ($a_1A_1$ units, $a_2A_2$ units, ... $a_nA_n$ units, with $a_1+a_2+\ldots+a_n=a$), as explained above. In this case, the different "R" substituents are called $R_1, \ldots R_n$, the different "x" numbers are called $x_1, \ldots x_n$, the different "X" substituents are called, $X_1, \ldots X_n$, and the numbers of the various different units are designated by $a_1, a_2, \ldots a_n$, with $a_1+a_2+\ldots a_n=a$.

Similarly, in a given polymer, the polymer can have several different B units, several different C units and several different D units, for example, up to 10 different B, C or D units, and generally two or three different B or C or D units. Accordingly, there is employed for the substituents a nomenclature analogous to that adopted for the A units, that is to say, $R'_1, R'_2 \ldots R'_n, b_1, b_2 \ldots b_n$, etc.

Among the dye products of the present invention, there are, in particular, those for which X represents the residue of a dye molecule selected from the azo dyes, azinic dyes, aminotriphenylmethane dyes, anthraquinone dyes, nitro dyes or dyes derived from indophenols, indoanilines, indoamines and the like.

Among the polymers of the present invention, are those, principally, for which the substituents have the following values, taken singly or in combination:

R represents hydrogen or alkyl having 1-4 carbon atoms;

R' represents hydrogen, lower hydroxy alkyl, such as β-hydroxyethyl or γ-hydroxypropyl, alkyl such as methyl, ethyl, propyl, butyl, hexyl, octyl, decyl, dodecyl, tetradecyl, pentadecyl, hexadecyl or octadecyl, or alkenyl such as octadecenyl;

R" represents hydrogen, hydroxyalkyl such as those mentioned above, or alkyl having 1-4 carbon atoms, or R' and R" together represent —$(CH_2)_5$— or —$(CH_2)_2$—O—$(CH_2)_2$—;

R''' represents hydrogen or alkyl having 1-4 carbon atoms;

$R_I$, $R_{II}$ and $R_{III}$ each independently represent alkyl or alkenyl, having up to 18 carbon atoms; and $Z^\ominus$ represents an organic anion such as a methosulfate or ethosulfate anion, or a mineral anion such as a bromide, an iodide, a chloride or the like;

x is a whole number ranging from 2 to 6, and is, preferably, equal to 2 or 3; and y is preferably equal to 2 or 3.

The X substituent represents the residue of a dye molecule and is, principally, one of the following residues:

(1) the residue of an anthraquinone dye having the formula

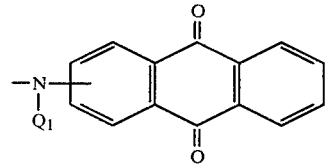

wherein, $Q_1$ represents hydrogen, lower alkyl or lower hydroxy alkyl, and the aromatic rings can have one or more substituents such as amino, amino substituted, for example, by one or two lower alkyl groups such as methyl, hydroxy, sulfonamide, amide, halogen, nitro, sulfonate or carboxylate;

(2) the residue of a nitro dye of the formula,

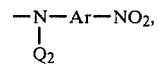

wherein $Q_2$ represents hydrogen, lower alkyl or lower hydroxyalkyl; and Ar represents an aromatic group, such as phenyl, optionally substituted, for example, by an amino group, a substituted amino group, i.e. principally (lower alkyl)-amino, by lower alkyloxy, or by hydroxy;

(3) the residue of an azo dye molecule of the formula,

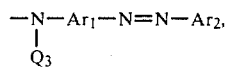

wherein $Q_3$ represents hydrogen, lower alkyl or hydroxyalkyl; $Ar_1$ and $Ar_2$ each independently represent an aromatic group, substituted or not, such as a benzenic, naphthalenic, indazolic, benzimidazolic, thiazolic, imidazolic, quinolinic, pyridinic or benzothiazolic group;

(4) The residue of an azinic dye such as an oxazinic or thiazinic groups; and (5) The residue of a triphenylmethane dye.

In the polymers of the present invention, the various units can have an L or D configuration or can be found present in the form of mixtures of stereoisomers.

The invention also relates to a process for preparing the dye polymers mentioned above. This process comprises reacting polydehydroaspartic acid of formula (V):

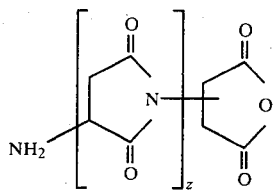

wherein z is a whole number ranging from 15 to 500, with at least one amine of formula II defined above, at a rate of $m_1$ moles of amine II per mole of polydehydroaspartic acid, $m_1$ being a whole or decimal number varying from 1 to $z+1$ and being able even to be greater than $z+1$ in the case where an excess of amine II is used. In the case where $m_1$ is lower than z, the product obtained is reacted with one or more amines of formula III and/or IV, such as defined above, and/or the product obtained is treated with an alkali base or alkaline earth base.

The polydehydroaspartic acid can be obtained in accordance with the methods described in the literature. Thus, in accordance with Fox et coll., Analytical Method of Protein Chemistry, Vol. IV, p. 127, ed. P. Alexander and H. P. Lundgreen, Pergamon Press, polydehydroaspartic acid is prepared by heating aspartic acid in the presence or not of phosphoric acid; in accordance with Kovacs et coll., J. Org. Chem. 26, 1081 (1961) polydehydroaspartic acid is obtained by prolonged heating, 100 hours, of aspartic acid in tetralin or under a vacuum; and in accordance with French patent 70.24831 the polydehydroaspartic acid is prepared by heating aspartic acid in the presence of phosphoric acid under a vacuum at 170°–200° C. by assuring a constant renewal of the reaction mass surface.

Polydehydroaspartic acid can also be obtained by carrying out the polymerization of aspartic acid in the presence of a solvent having a high boiling point, such as diphenyl ether, and a strong acid ion exchange resin, for example, "Amberlite IR 120H" at a temperature from 200°–230° C. under ambient pressure. Polydehydroaspartic acid is thus obtained in a brief period of time and in practically quantitative yields.

The polymers of the invention are dye products which can be used in compositions for dyeing fibers and, principally, in compositions for dyeing keratinic fibers and, particularly, in hair dye compositions.

These hair dye compositions provide the following advantages.

They lead to the attainment of a coloration which is less selective than that obtained with nonpolymeric dyes, these latter being fixed, preferentially, on the most sensitized portions of the hair, which, as a consequence, results in a heterogeneous coloration.

On the other hand, it is also known that the dyeing of keratinic fibers is usually effected with dyes of relatively low molecular weight. Such dyes have a tendency to penetrate the interior of the fiber. On the other hand, the dye products of the present invention remain, because of their molecular dimensions, on the exterior of the keratinic fiber. One of the advantages provided by the present invention is that the new dye polymers are not toxic when they are used on the hair, or they have a toxicity significantly lower than that of nonpolymer dyes, since the dye or dye precursor groups are not found in a free state but are made part of the polymer which, because of their large molecular dimensions, essentially cannot diffuse through the skin. This advantage is very important in the field of dyeing human hair.

The present invention also relates to a dye composition comprising at least one dye product defined above.

However, when the polymer has no dye groups but only dye precursors, the dye precursor must be transformed into a dye in accordance with known methods, before use, by the action of an appropriate reagent.

The dye compositions according to the present invention generally contain from 0.005 to 15 weight percent, and preferably, from 0.02 to 8 weight percent, of at least one polymer dye, relative to the total weight of the composition.

These compositions can also contain other dyes such as azo dyes, anthraquinone dyes, nitrobenzene dyes, diaminoquinones, indophenols, indoanilines, indamines, diphenylamines, oxidation bases or couplers.

These dye compositions can also include at least one of the following agents: alkalizing or acidifying agents, solvents, thickening agents, surfactants, solar filters (sunscreens), optical blueing agents, antioxidants, sequesterants, processing agents and perfumes.

The compositions according to the present invention are generally provided in the form of solutions, principally aqueous or hydroalcoholic solutions, creams, gels, foaming liquids or milks. These compositions can be packaged in bottles, tubes or aerosol containers.

The dye compositions of the present invention are principally dye compositions for the hair which contain a dye vehicle or support conventionally employed to provide the hair dye compositions in the forms indicated above, as well as additives conventionally used in such capillary lotions.

More precisely, the dye compositions of the present invention can be temporary, semi-permanent or permanent dye compositions.

The principles of formulating such dye compositions are described in cosmetology works, in particular, the work of Edwin Sidi and Charles Zviak, Problems Capillaries, "Etude Clinique, Biologique, Physico-chemique de la Chevelure Feminine," Paris (Gauthier Villars), 1966.

Temporary dye compositions include, for example: aqueous or hydroalcoholic solutions, either ready-for-use, or concentrates to be diluted at the time of use; lotions for application after shampooing; dye shampoos; and hair setting dye lotions.

The concentrates are diluted, for example, with lukewarm water before application. Lotions to be applied after shampooing can be foaming or non-foaming lotions.

The dye shampoos also contain a detergent and, depending on the circumstances, such an operation can be concluded, if necessary, by rinsing with water.

Hair setting dye lotions contain, in an aqueous or hydroalcoholic solution, in addition to the dye polymers described above, a film-forming polymer conventionally employed in hair setting compositions. For example, there can be employed such film-forming polymers as polyvinylpyrrolidone, copolymers of vinylpyrrolidone and vinyl acetate, copolymers of vinyl acetate and crotonic acid, and the like.

Semi-permanent dye compositions are those capable of adding to the natural color of the hair a lighter shade and of imparting natural glints to white hair when they are present in relatively weak amounts. The application of these compositions necessitates neither previous bleaching nor simultaneous bleaching of the hair.

Semi-permanent dye compositions also contain components which permit them to be provided principally in the form of lotions, foaming lotions or shampoos.

In accordance with a particular embodiment of the present invention, these semi-permanent dye compositions contain organic solvents such as alcohols, for example, benzyl alcohol, and glycol ethers, such as the cellosolves (ethyl cellosolve, butyl cellosolve) etc.

The permanent dye compositions are principally oxidation dye compositions which contain oxidation dyes in addition to the dye polymers mentioned above. Such compositions must be mixed before use with an oxidizing agent such as hydrogen peroxide in conventional amounts and in accordance with usual procedures. In such compositions, the dye polymers of the present invention provide particular shades or glints.

These oxidation dye compositions can be provided in the form of gelifiable liquid compositions or in the form of creams.

These compositions in the form of creams can also contain, for example, fatty alcohols, oxyethylenated or sulfated fatty alcohols, fatty amides and the like.

The gelifiable compositions can be, for example, oxyethylenated non-ionic solutions, in particular, polyethoxylated alkyl phenols. On dispersion with hydrogen peroxide, such compositions give a gel.

The present invention also encompasses, in this case, a two-part composition, the two parts being mixed at the time of use and being packaged in an appropriate container. The first part comprises the composition containing the dye polymer or dye precursor and the oxidation dyes, while the second part contains an oxidizing agent such as hydrogen peroxide, in an amount sufficient to transform by oxidative condensation the oxidation dyes of the said first part into colored compounds. It is to be understood that the container for such a two-part composition carries directions for the use of such a composition.

The present invention also relates to a process for dyeing keratinic fibers, and principally human hair, comprising applying to said fibers, for a time sufficient to obtain the desired color, at least one dye polymer as defined above, principally in the form of a composition such as defined above.

EXAMPLES OF PREPARATION

Example 1—Preparation of a polymer of formula (I) wherein $b=0$, $d=0$, $a:c=25:75$, $R=R'''=H$, $x=2$, $y=3$, $Y=-N(CH_3)_3$, $X=2$-anthraquinonyl amino and $Z^\ominus=$ methosulfate.

9.7 g of polydehydroaspartic acid are dissolved in 50 cc of dimethylformamide. To this solution there are added 7 g of 2-(2-amino ethyl) anthraquinone in solution in 100 cc of dimethylformamide. The resulting mixture is heated at 100° C. for 8 hours. The resulting dye polymer is precipitated with acetic acid, washed with alcohol and dried, thus yielding 11.5 g of orange yellow product. The colored polymer thus obtained is re-dissolved in 50 cc of dimethylformamide. To this solution there are added 5.2 g of 1,3-N,N-dimethyl diamino propane and the mixture is heated for 6 hours at 80° C. There are then slowly added 6.9 g of dimethyl sulfate and the mixture is stirred for 3 hours at ambient temperature.

The resulting dye polymer is precipitated with isopropanol, washed and dried under a vacuum at 100° C., thereby yielding 20.3 g of an orange polymer which is very soluble in water.

Thin layer chromatography (silica gel, acetic acid-methanol eluent) shows that the polymer does not contain any non-grafted dye.

EXAMPLES 2 and 3

In an analogous manner the following colored polymers of formula (I), wherein $b=d=0$, $y=3$, $R=R'''=H$, $Y=$ trimethyl ammonium and $Z^\ominus=$ methosulfate are obtained.

| Example No. | x | X | a:c | Color |
| --- | --- | --- | --- | --- |
| 2 | 3 | 4-methylamino-1-anthraquinonyl amino | 30:70 | Blue |
| 3 | 3 | 1-anthraquinonyl amino | 30:70 | Red |

Example 4—Polymer of formula (I) wherein:
$a_1:a_2:a_3:c=10.5:12.5:7:30$, $b=d=0$,
$R_1=R_2=R_3=R'''=H$, $x_1=x_2=y=3$, $x_3=2$,
$X_1=1$-anthraquinonyl amino,
$X_2=4$-methylamino-1-anthraquinonyl amino,
$X_3=2$-anthraquinonyl amino, $Y=$ trimethyl ammonium and $Z^\ominus=$ methosulfate.

Stage A 9.7 g of polydehydroaspartic acid are dissolved in 50 cc of dimethylformamide. To this solution there are added 2.93 g of 1-(3-amino propyl) amino anthraquinone, 3.92 g of 1-(3-amino propyl) amino-4-methylamino anthraquinone and 1.83 g of 2-(2-amino ethyl) amino anthraquinone in solution in 180 cc of dimethylformamide. This mixture is heated for 24 hours at 100° C. 200 cc of dimethylformamide are evaporated off under reduced pressure and the polymer is precipitated with ethanol. After washing the resulting polymer with ethanol and drying it under a vacuum, there are obtained 12.55 g of a blue gray polymer product.

Stage B. The polymer thus obtained is re-dissolved in 200 cc of dimethylformamide. To this solution there are added 4.65 g of 1,3-N,N-dimethyl diamino propane. The mixture is heated at 100° C. for 6 hours. Then there are added 5.67 g of dimethyl sulfate and the mixture is stirred for 4 hours at ambient temperature.

The colored polymer obtained by precipitation with isopropanol is washed and dried and is in the form of a very water soluble gray powder.

Example 5—Polymer of formula (I) wherein:
$a:d=15:85$, $b=c=0$, $R=H$, $x=2$, $M=Na$ and
$X=4$-methoxy-2-nitro anilino.

Stage A

Preparing the dye
19.4 g of polydehydroaspartic acid are dissolved in 130 cc of dimethylformamide. To this solution are added 6.33 g of 4-(2-amino ethyl) amino-3-nitro anisole in solution in 50 cc of dimethyl formamide. The mixture is heated at 90° C. for 6 hours. After precipitation using 200 cc of acetic acid, washing with ethanol and drying, there are obtained 20 g of a red-orange product.

Stage B

The polymer thus obtained is re-dissolved in 170 cc of dimethylformamide. To this solution there are added 13.6 cc of NaOH in 30% aqueous solution. The mixture is stirred for 20 hours at ambient temperature. The colored polymer which is precipitated by the addition of ethanol is washed and then dried under a vacuum. 24 g of a very water soluble red powder are obtained.

Example 6—Polymer of formula (I) wherein:
a:c=15.85, b=d=0, R=R'''=H, x=2, y=3, Y=trimethyl ammonium, $Z^-$=methosulfate, and X=4-methoxy-2-nitro anilino.

Stage A

Preparation of the dye
The procedures set forth in Stage A of Example 5 are repeated.

Stage B 20 g of the polymer thus obtained are dissolved in 170 cc of dimethylformamide. To this solution are added 13.67 g of 1,3-N,N-dimethyl diamino propane. The mixture is heated at 80° C. for 5 hours. Then 16.88 g of dimethyl sulfate are added and the reaction mixture is left for 1 hour at ambient temperature. After precipitation with isopropanol, washing and drying, the colored polymer is obtained in the form of a very water soluble orange powder.

Example 7—Polymer of formula (I) wherein:
a:b=15:85, c=d=0, R=R'=H, R''=β-hydroxyethyl, x=2 and X=4-methoxy-2-nitro anilino.

Stage A

Preparation of the dye
The procedures set forth in Stage A of Example 5 are repeated.

Stage B 19 g of the polymer thus obtained are dissolved in 150 cc of dimethylformamide. To this solution are added 7.68 g of monoethanolamine. The mixture is then heated at 90° C. for 6 hours. After precipitation with ethanol, washing and drying under a vacuum, 19.6 g of a colored polymer in the form of a very water soluble red powder are obtained.

Example 8—Polymer of formula (I) wherein:
$a:b_1:b_2$=15:76.5:8.5, c=d=0, $R=R''_1$=H, $R'_1$=dodecyl, $R'_2=R''_2$=β-hydroxyethyl, x=2 and X=4-amino-3-nitro anilino.

Stage A 81.1 g of polydehydroaspartic acid are dissolved in 425 cc of dimethylformamide. To this solution are added 24.6 g of 4-(2-amino ethyl) amino-2-nitro aniline in solution in 140 cc of dimethylformamide. This mixture is heated at 90° C. for 6 hours. After precipitation by 1 liter of isopropanol, washing with alcohol and drying, 140 g of a violet product are obtained.

Stage B 37 g of the polymer obtained above are dissolved in 150 cc of dimethylformamide. To this solution are added 5.08 g of dodecylamine in solution in 20 cc of dimethylformamide. This mixture is heated for 12 hours at 90° C. There are then added 26 g of diethanolamine and the resulting mixture is again heated for 30 hours at 90° C. The dimethyl formamide is distilled off under reduced pressure. The dry dye polymer thus obtained is re-dissolved in 150 cc of isopropanol and precipitated by the addition of the same volume of isopropyl ether.

After washing with a 1:1 mixture of isopropanol and isopropyl ether and drying under reduced pressure, 40 g of a very water soluble purple colored polymer are obtained.

Example 9—Polymer of formula (I) wherein:
$a:b_1:b_2$=15:76.5:8.5, c=d=0, $R=R''_2$=H, x=2, $R'_1+R''_1$=—(CH$_2$)$_5$—, $R'_2$=octadecyl and X=4-amino-3-nitro anilino.

37 g of the polymer obtained in Example 8 (Stage A) are dissolved in 160 cc of dimethylformamide. 7.37 g of octadecylamine are added thereto and the mixture is heated for 10 hours at 90° C. There are then added 21 g of piperidine and the mixture is again heated for 50 hours at 90° C. The reaction mixture is left to cool and the polymer is precipitated by adding 500 cc of isopropyl ether. After washing with isopropyl ether and drying under reduced pressure, 47 g of a very water soluble purple product are obtained.

Example 10—Polymer of formula (I) wherein:
a:b:c=15:8.5:76.5, x=2, y=3, d=0, R=R''=R'''=H, R'=octadecene-9-yl-1, Y=dimethylethyammonium, $Z^\ominus$=ethosulfate and X=4-amino-3-nitro anilino.

20 g of the polymer obtained in Example 8 (Stage A), are dissolved in 110 cc of dimethylformamide. 3.96 g of oleylamine are then added and the mixture is heated for 17 hours at 90° C. 13.6 g of 1,3-N,N-dimethyldiamino propane are then added and this mixture is heated for 50 hours at 90° C.

The reaction mixture is left to cool and the dye polymer is precipitated by adding 500 cc of a 1:1 isopropanol isopropyl ether mixture.

After filtering and washing with isopropyl ether, the product is re-dissolved in 150 cc of dimethylformamide. 10 cc of diethyl sulfate are then added and the mixture is heated at 90° C. for 7 hours. The dimethylformamide is distilled off under reduced pressure and the polymer dye is washed twice with 100 cc of dichloromethane.

After drying, 16 g of a very water soluble red powder are obtained.

Example 11—Polymer of formula (I) wherein:
a:b=85:15, c=d=0, x=2, R=R'=H, R''=β=hydroxyethyl and X=

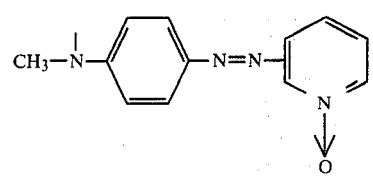

Stage A 1.98 g of polydehydroaspartic acid are dissolved in 10 cc of dimethylformamide. There is then added 0.81 g of 4'-N(2-amino ethyl) N-methyl amino-1'-benzene azo: 2 pyridine N-oxide in solution in 30 cc of dimethylformamide. This mixture is heated for 15 hours at 90° C. Then the polymer is precipitated by adding 200 cc of isopropanol.

After washing with isopropanol and drying under reduced pressure, 3 g of a red product are obtained.

Stage B 2.28 g of the polymer obtained above in Stage A are dissolved in 40 cc of dimethylformamide. 1.26 g of monoethanolamine are then added and the mixture is heated at 90° C. for 20 hours. The reaction mixture is left to cool and the dye polymer is precipitated by adding 200 cc of isopropanol.

After washing with isopropanol and drying under reduced pressure, 2 g of a very water-soluble red product are obtained.

Example 12—Polymer of formula (I) wherein:
$a:b=15:85$, $c=d=0$, $R=H$, $x=2$,
$R+R''=-(CH_2)_2-O-(CH_2)_2-$ and
$X=$ 4-amino-3-nitro-$N_1$-methylanilino.

49 g of polydehydroaspartic acid are dissolved in 200 cc of dimethylformamide. To this solution are added 15.75 g of 4-N-(2-amino ethyl)-N-methylamino-2-nitro aniline. The mixture is heated at 90° C. for 5 hours. 37 g of morpholine are then added and the mixture is again heated from 20 hours at 90° C.

The dye polymer is precipitated by adding isopropyl ether. After washing with isopropyl ether and drying under reduced pressure, 71 g of a dye polymer which is very soluble in water and which has a deep purple color are obtained.

Example 13—Polymer of formula (I) wherein:
$a:c=50:50$, $b=d=0$, $R=R'''=H$, $x=y=3$,
$Y=$ trimethylammonium, $Z^{\ominus}=$ methosulfate and
$X=$ 1-anthraquinonyl amino.

This dye, obtained in accordance with procedures analogous to those described in Example 1, is a red colored polymer.

Example 14—Polymer of formula (I) wherein:
$a:c=12.88$, $b=d=0$, $R=R'''=H$, $x=2$, $y=3$,
$Y=$ trimethylammonium, $Z^{\ominus}=$ methosulfate and
$X=$ 2-anthraquinonyl amino.

This dye polymer, obtained in accordance with procedure analogous to those described in Example 1, is an orange red polymer.

EXAMPLES OF COMPOSITIONS

Example C$_1$—A hair setting lotion is prepared by admixing the following components:

| | |
|---|---|
| Polymer of Example 2 | 0.5 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethylhydroxy ethylammonium bromide wherein the alkyl is the residue of copra | 0.2 g |
| Ethyl alcohol (96°), sufficient for 50° | |
| Water, sufficient amount for | 100 cc |

When applied as a hair setting lotion on natural or dyed, black or brown hair, this composition, which has a spontaneous pH of 7, imparts thereto very esthetic bluish glints.

Example C$_2$—A composition is prepared by admixing the following components:

| | |
|---|---|
| Polymer of Example 8 | 0.3 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxy ethylammonium bromide, wherein the alkyl is a copra residue | 0.2 g |
| Ethyl alcohol, 96°, sufficient amount for 50° | |
| Citric acid, sufficient amount for pH 7 | |
| Water, sufficient amount for | 100 cc |

This composition is applied on light chestnut colored hair. On drying, the hair exhibits pretty nacreous glints.

Example C$_3$—A composition is prepared by admixing the following components:

| | |
|---|---|
| Polymer of Example 11 | 0.25 g |
| Copolymer of vinyl pyrrolidone/vinyl acetate (60/40) | 0.5 g |
| Quaternized polyvinyl pyrrolidone, sold under the name "GAFQUAT 734" | 0.4 g |
| Alkyl dimethyl hydroxy ethylammonium bromide where said alkyl is the residue of copra | 0.2 g |
| Ethyl alcohol, 90°, sufficient amount for 50° | |
| Citric acid, sufficient amount for pH 7 | |
| Water, sufficient amount for | 100 cc |

This composition is a hair setting lotion which facilitates untangling of the hair and imparts to natural or dyed blond hair a delicate coppery shade.

Example C$_4$—A composition is prepared by admixing the following components:

| | |
|---|---|
| Polymer of Example 6 | 0.3 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxy ethylammonium bromide wherein the alkyl moiety is a copra residue | 0.2 g |
| Ethyl alcohol, 96°, sufficient for 50° | |
| Citric acid, sufficient amount for pH 7 | |
| Water, sufficient amount for | 100 cc |

This composition is applied to the hair before styling it.

This lotion imparts to light or bleached hair golden glints with particularly becoming coppery specks.

Example C$_5$—A composition is prepared by admixing the following components:

| | |
|---|---|
| Polymer of Example 13 | 0.05 g |
| Copolymer of vinyl pyrrolidone/vinyl acetate, 60/40 | 0.4 g |
| Copolymer of vinyl acetate/crotonic acid, 90/10 | 0.4 g |
| Benzyl alcohol | 10 g |

-continued

| | |
|---|---|
| Ethyl alcohol, 96°, sufficient amount for 70° | |
| Monoethanolamine, sufficient amount for pH 7 | |
| Water sufficient amount for | 100 cc |

When this hair setting lotion is applied to natural or dyed brown hair, the hair exhibits very esthetic light mahogany glints.

Example $C_6$—A composition is prepared by admixing the following components:

| | |
|---|---|
| Polymer of Example 4 | 0.3 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxy ethylammonium bromide wherein the alkyl is the residue of copra | 0.2 g |
| Ethyl alcohol, 96°, sufficient for 50° | |
| Triethanolamine, sufficient amount for pH 7 | |
| Water, sufficient amount for | 100 cc |

This hair setting lotion when applied to natural chestnut colored hair imparts thereto mahogany chestnut glints.

Example $C_7$—A composition is prepared by admixing the following components:

| | |
|---|---|
| Polymer of Example 9 | 0.23 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxy ethylammonium bromide wherein the alkyl is the residue of copra | 0.2 g |
| Ethyl alcohol, 96°, sufficient for 50° | |
| Citric acid, sufficient amount for pH 7 | |
| Water, sufficient amount for | 100 cc |

This hair setting lotion when applied to natural or dyed light chestnut colored hair, imparts thereto pearly beige glints which are particularly becoming.

Example $C_8$—A composition is prepared by admixing the following components:

| | |
|---|---|
| Polymer of Example 14 | 2 g |
| Copolymer of vinyl pyrrolidone/vinyl acetate, 60/40 | 0.5 g |
| Quaternized polyvinyl pyrrolidone sold under the name "GAFQUAT 734" | 0.4 g |
| Alkyl dimethyl hydroxy ethylammonium bromide wherein the alkyl is the residue of copra | 0.2 g |
| Ethyl alcohol, 96°, sufficient for 50° | |
| Triethanolamine, sufficient amount for pH 7 | |
| Water, sufficient amount for | 100 cc |

The above hair setting lotion composition is applied to deep blond hair. After drying, the hair exhibits pretty golden coppery glints.

Example $C_9$—A composition is prepared by admixing the following components:

| | |
|---|---|
| Polymer of Example 12 | 0.7 g |
| Copolymer of vinyl pyrrolidone/vinyl acetate, 60/40 | 2 g |
| Copolymer of vinyl acetate/crotonic acid, 90/10 | 2 g |
| Trimethyl cetyl ammonium bromide | 0.2 g |
| Ethyl alcohol, 96°, sufficient for 50° | |
| Triethanolamine, sufficient amount for pH 7 | |
| Water, sufficient amount for | 100 cc |

This composition when applied to deep blond hair as a hair setting lotion, imparts thereto very esthetic mahogany glints.

Example $C_{10}$—A composition is prepared by admixing the following components:

| | |
|---|---|
| Polymer of Example 6 | 1.2 g |
| Polymer of Example 2 | 0.06 g |
| 1-N-($\gamma$-aminopropyl) amino) anthraquinone hydrochloride | 0.1 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxy ethylammonium bromide wherein the alkyl is the residue of copra | 0.2 g |
| Ethyl alcohol, 96°, sufficient for 50° | |
| Triethanolamine, sufficient amount for pH 7 | |
| Water, sufficient amount for | 100 cc |

This composition is applied to natural or dyed brown colored hair. After setting the hair and drying it, the hair exhibits very becoming mahogany glints.

Example $C_{11}$—A composition is prepared by admixing the following components:

| | |
|---|---|
| Polymer of Example 10 | 0.08 g |
| 4-N-methyl amino-1-N-($\gamma$-aminopropyl) amino anthraquinone hydrochloride | 0.04 g |
| 2-N-($\beta$-amino ethyl) amino anthraquinone hydrochloride | 0.02 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxyethyl ammonium bromide wherein the alkyl is the residue of copra | 0.2 g |
| Ethyl alcohol, 96°, sufficient for 50° | |
| Citric acid, sufficient amount for pH 7 | |
| Water, sufficient amount for | 100 cc |

When this hair setting lotion is applied to gray hair having less than 50% white hair, there is obtained after drying, ash blue glints which is a most beautiful effect.

Example $C_{12}$—A composition is prepared by admixing the following components:

| | |
|---|---|
| Polymer of Example 2 | 0.05 g |
| Polymer of Example 6 | 0.3 g |
| Polymer of Example 8 | 0.5 g |
| Copolymer of vinyl pyrrolidone/vinyl acetate, 60/40 | 0.5 g |
| Quaternized polyvinyl pyrrolidone, sold under the name "GAFQUAT 734" | 0.4 g |
| Alkyl dimethyl hydroxy ethyl ammonium bromide wherein the alkyl is the residue of copra | 0.2 g |
| Ethyl alcohol, 96°, sufficient for 50° | |
| Citric acid, sufficient amount for pH 7 | |
| Water, sufficient amount for | 100 cc |

This composition is a hair setting lotion which is applied to natural or dyed light chestnut colored hair. It imparts thereto very pretty pearly glints.

Example C₁₃—A composition is prepared by admixing the following components:

| | |
|---|---|
| Polymer of Example 11 | 0.01 g |
| CI Basic Violet 3 (CI 42555) | 0.003 g |
| Picramic acid | 0.023 g |
| Light acetoquinone black, BN 1150 (CFMC) | 0.1 g |
| Copolymer of vinyl pyrrolidone/ vinyl acetate, 60/40 | 0.5 g |
| Quaternized polyvinyl pyrrolidone, sold under the name "GAFQUAT 734" | 0.4 g |
| Alkyl dimethyl hydroxy ethyl ammonium bromide wherein the alkyl is the residue of copra | 0.2 g |
| Ethyl alcohol, 96°, sufficient for 50° | |
| Citric acid, sufficient amount for pH 7 | |
| Water, sufficient amount for | 100 cc |

Blond hair treated with such a hair setting lotion has, after drying, particularly esthetic beige glints.

Example C₁₄—A composition is prepared by admixing the following components:

| | |
|---|---|
| Polymer of Example 2 | 0.1 g |
| Polymer of Example 6 | 0.7 g |
| Polymer of Example 9 | 0.18 g |
| Ethyl cellosolve | 10 g |
| Trimethyl cetyl ammonium bromide | 1.5 g |
| Synthetic C₁₃-C₁₅ linear fatty alcohol having 2.8 moles of ethylene oxide, sold under the name "UKANIL 25" | 3 g |
| Synthetic C₉-C₁₁ linear fatty alcohol having 6 moles of ethylene oxide, sold under the name "UKANIL 43" | 2 g |
| Homogentisic acid | 0.5 g |
| Monoethanol amine, sufficient amount for pH 7 | |
| Water, sufficient amount for | 100 g |

This composition when applied for 5 minutes on bleached hair imparts to the hair, after rinsing and drying, golden beige glints which resist shampooing.

Example C₁₅—A composition is prepared by admixing the following components:

| | |
|---|---|
| Polymer of Example 6 | 0.55 g |
| 4-N',N'-(methyl, β-hydroxyethyl) amino-2-nitro, N-methyl aniline | 0.07 g |
| 4-N-(β-hydroxyethyl) amino-3-nitro phenol | 0.025 g |
| Ethyl cellosolve | 10 g |
| Trimethyl cetyl ammonium bromide | 1.5 g |
| Synthetic C₁₃-C₁₅ linear fatty alcohol having 2.8 moles of ethylene oxide, sold under the name "UKANIL 25" | 3 g |
| Synthetic C₉-C₁₁ linear fatty alcohol having 6 moles of ethylene oxide, sold under the name "UKANIL 43" | 2 g |
| Homogentisic acid | 0.5 g |
| Monoethanolamine, sufficient amount for pH 7 | |
| Water, sufficient amount for | 100 g |

This composition when applied for 5 minutes to previously bleached hair, imparts thereto after rinsing and drying a coppery shade which persists after shampooing.

Example C₁₆—A composition is prepared by admixing the following components:

| | |
|---|---|
| Polymer of Example 4 | 2.5 g |
| Polymer of Example 5 | 0.1 g |
| Sodium lauryl ether sulfate, 30% active material, sold under the name "SACTIPON 8533" | 25 g |
| Diethanolamide of the fatty acids of coconut, sold under the name of "COMPERLAN KD" | 5 g |
| Butyl cellosolve | 1 g |
| Citric acid, sufficient amount for pH 6 | |
| Water, Sufficient amount for | 100 g |

This composition when applied for 15 minutes to hair having 70-100% white hair, produces, after rinsing and drying, an excellent non-yellowing natural gray color.

Example C₁₇—A composition is prepared by admixing the following components:

| | |
|---|---|
| Polymer of Example 9 | 0.08 g |
| CI Basic Green 5 (CI 52020) | 0.01 g |
| 5-nitro orthoaminophenol | 0.20 g |
| 4-N-methylamino-2-nitro aniline | 0.44 g |
| Sodium lauryl ether sulfate, 30% active material, sold under the name "SACTIPON 8533" | 25 g |
| Diethanolamide of the fatty acids of coconut, sold under the name "COMPERLAN KD" | 5 g |
| Butyl cellosolve | 1 g |
| Citric acid, sufficient amount for pH 6 | |
| Water, sufficient amount for | 100 g |

This composition, when applied for 15 minutes to natural deep blond hair, produces a very esthetic coppery chestnut shade.

Example C₁₈—A composition is prepared by admixing the following components:

| | |
|---|---|
| Polymer of Example 11 | 0.6 g |
| Paratoluylenediamine | 0.08 g |
| Paraaminophenol | 0.09 g |
| Resorcinol | 0.09 g |
| Metaaminophenol | 0.05 g |
| Hydroquinone | 0.1 g |
| Nonylphenol oxyethylenated with 4 moles of ethylene oxide, sold under the name "REMCOPAL 334" | 22 g |
| Nonylphenol oxyethylenated with 9 moles of ethylene oxide, sold under the name "REMCOPAL 349" | 22 g |
| Butyl cellosolve | 8 g |
| Propyleneglycol | 8 g |
| Ethylene diamine tetraacetic acid | 0.2 g |
| Ammonia (22° Be) | 4 cc |
| Sodium bisulfite (35° Be) | 1 cc |
| Water, sufficient amount for | 100 g |

At the time of use, 40 g of this composition are mixed with 40 g of H₂O₂ (titrated at 6%). The mixture is a gel which, when applied for 30 minutes on light blond hair, provides after shampooing and drying, a delicate, very light blond shade with golden glints.

Example C₁₉—A composition is prepared by admixing the following components:

| | |
|---|---|
| Polymer of Example 2 | 0.3 g |
| Paratoluylenediamine | 0.35 g |
| Paraaminophenol | 0.09 g |
| Resorcinol | 0.25 g |
| Metaaminophenol | 0.1 g |
| Nonylphenol oxyethylenated with 4 moles of ethylene oxide, sold | |

| | |
|---|---|
| under the name "REMCOPAL 334" | 22 g |
| Nonylphenol oxyethylenated with 9 moles of ethylene oxide, sold under the name "REMCOPAL 349" | 22 g |
| Butyl cellosolve | 8 g |
| Propyleneglycol | 8 g |
| Ethylene diamine tetraacetic acid | 0.2 g |
| Ammonia (22° Be) | 4 cc |
| Sodium bisulfite (35° Be) | 1 cc |
| Water, sufficient amount for | 100 g |

This liquid is mixed, weight for weight, with $H_2O_2$ (6%) just before dyeing the hair. 80 g of the resulting gel are applied to light chestnut colored hair. The shade obtained, after shampooing and drying, is a deep ash blond color.

Example $C_{20}$—A composition is prepared by admixing the following components:

| | |
|---|---|
| Polymer of Example 6 | 0.5 g |
| N-($\beta$-methoxyethyl) paraphenylene diamine | 0.06 g |
| Paraaminophenol | 0.3 g |
| N-methyl paraaminophenol | 0.15 g |
| Resorcinol | 0.15 g |
| Metaaminophenol | 0.03 g |
| 2-methyl-5-N-($\beta$-hydroxyethyl) amino phenol | 0.05 g |
| 2,4-diamino phenoxy ethanol dihydrochloride | 0.02 g |
| 4-N-($\beta$-hydroxyethyl) amino-3-nitro anisole | 0.23 g |
| Nonylphenol oxyethylenated with 4 moles of ethylene oxide, sold under the name "REMCOPAL 334" | 22 g |
| Nonylphenol oxyethylenated with 9 moles of ethylene oxide, sold under the name "REMCOPAL 349" | 22 g |
| Butyl cellosolve | 8 g |
| Propylene glycol | 8 g |
| Ethylene diamine tetraacetic acid | 0.2 g |
| Ammonia (22° Be) | 4 cc |
| Sodium bisulfite (35° Be) | 1 cc |
| Water, sufficient amount for | 100 g |

40 g of this composition are admixed with 40 g of $H_2O_2$ (6%), the mixture being made at the time of use. The resulting mixture is applied on light blond hair and after a 30-minute contact period therewith, the hair is rinsed, shampooed and dried. The hair is thus dyed a very esthetic, slightly golden very light blond color.

Example $C_{21}$—A composition is prepared by admixing the following components:

| | |
|---|---|
| Polymer of Example 8 | 0.5 g |
| Polymer of Example 9 | 0.35 g |
| Paraphenylenediamine | 0.2 g |
| 2-methyl-5-methoxy paraphenylene diamine | 0.03 g |
| Paraaminophenol | 0.02 g |
| 2,4-diamino anisole sulfate trihydrate | 0.015 g |
| Resorcinol | 0.5 g |
| Metaaminophenol | 0.05 g |
| 6-hydroxy benzomorpholine | 0.02 g |
| Sodium lauryl sulfate | 15 g |
| Lauryl alcohol | 15 g |
| Ethylene diamine tetraacetic acid | 0.2 g |
| Thioglycolic acid | 0.3 cc |
| Ammonia (22° Be) | 11 cc |
| Water, sufficient amount for | 100 g |

This pink cream is mixed at the time of use, weight for weight, with an oxidizing milk containing 6% $H_2O_2$. The creamy mixture is easily applied to deep chestnut colored hair and left in contact therewith for 30 minutes. After shampooing and drying, a deep blond shade is obtained.

Example $C_{22}$—A composition is prepared by admixing the following components:

| | |
|---|---|
| Polymer of Example 5 | 0.6 g |
| N,N-di($\beta$-hydroxyethyl) paraphenylene diamine sulfate, monohydrate | 2 g |
| Paraaminophenol | 0.6 g |
| Resorcinol | 0.25 g |
| Metaaminophenol | 1 g |
| 2-methyl-5-N-($\beta$-hydroxyethyl) amino phenol | 0.9 g |
| N-($\alpha$-carbamylmethyl) metaamino phenol | 0.1 g |
| Sodium lauryl sulfate | 15 g |
| Lauryl alcohol | 15 g |
| Ethylene diamine tetraacetic acid | 0.2 g |
| Thioglycolic acid | 0.3 cc |
| Ammonia (22° Be) | 11 cc |
| Water, sufficient amount for | 100 g |

At the moment of use, 40 g of this cream are admixed with 40 g of an oxidizing milk of 6% $H_2O_2$. The resulting creamy mixture is applied to slightly sensitized blond hair. After shampooing and drying, a light ash blond shade is obtained.

What is claimed is:

1. A dye polymer, or a mixture thereof, comprising units of the formula

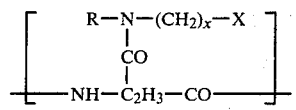

defined as A units wherein
R represents hydrogen or alkyl,
x is a whole number equal at least to 2, and
X represents the residue of a molecule of a dye or a dye precursor.

2. The polymer, or mixture thereof, of claim 1 which contains several different types of A units.

3. The polymer, or mixture thereof, of claim 2 which contains at most 10 different types of A units.

4. The polymer, or mixture thereof, of claim 3 which contains at most 3 different types of A units.

5. A polymer, or mixture thereof, of claim 1, having units of the formula

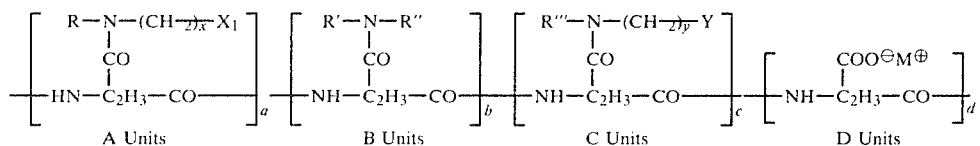

wherein:
R, x and X have the meanings given in claim 1,
R' represents hydrogen, lower hydroxy alkyl, alkyl having 1-18 carbon atoms or alkenyl having 2-18 carbon atoms,
R" represents hydrogen, lower hydroxy alkyl or lower alkyl, or R' and R" together with the nitrogen atom to which they are attached form a 5 or 6 chain ring, said ring optionally containing another heteroatom selected from oxygen and nitrogen,
y represents a whole number ranging from 2 to 6,
Y represents

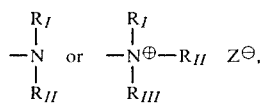

wherein $R_I$, $R_{II}$ and $R_{III}$ each independently represent hydrogen, alkyl having up to 18 carbon atoms or alkenyl having up to 18 carbon atoms, or $R_I$ and $R_{II}$ together with the nitrogen atom to which they are attached form a 5 or 6 chain ring, said ring optionally containing another heteroatom selected from nitrogen and oxygen,
$Z^\ominus$ is an anion,
R''' represents hydrogen or lower alkyl,
M represents hydrogen, an alkali metal atom or an alkaline earth metal half-atom, or M represents an ammonium ion derived from an amine selected from R—NH—$(CH_2)_x$—X, R'—NH—R" and R'''—NH—$(CH_2)_y$—Y, wherein R, x, X, R', R", R''', y and Y have the meanings given above,
a is a whole number above zero, and
b, c and d are whole numbers, including zero, such that the sum a+b+c+d ranges from 15 to about 500.

6. The polymer, or mixture thereof, of claim 5 which contains several different types of one or more of A units, B units, C units, or D units.

7. The polymer, or mixture thereof, of claim 1 wherein R represents hydrogen or alkyl having 1-4 carbon atoms, and x is a whole number ranging from 2 to 6.

8. The polymer, or mixture thereof, of claim 5 wherein
R' represents hydrogen, lower hydroxyalkyl selected from β-hydroxyethyl or γ-hydroxypropyl, alkyl selected from methyl, ethyl, propyl, butyl, hexyl, octyl, decyl, dodecyl, tetradecyl, hexadecyl or octadecyl, or octadecenyl,
R" represents hydrogen, lower hydroxyalkyl selected from β-hydroxyethyl or γ-hydroxypropyl or alkyl having from 1-4 carbon atoms, or R' and R" together represent —$(CH_2)_5$— or —$(CH_2)_2$—O—$(CH_2)_2$—.

9. The polymer, or mixture thereof, of claim 5 wherein $R_I$, $R_{II}$ and $R_{III}$ each independently represent alkyl having up to 18 carbon atoms, alkenyl having up to 18 carbon atoms, and $Z^\ominus$ represents an organic anion selected from methosulfate or ethosulfate, or an anion selected from bromide, iodide or chloride.

10. The polymer, or mixture thereof, of claim 5 wherein x and y are, independently, whole numbers equal to 2 or 3.

11. The polymer, or mixture thereof, of claim 5 wherein X represents a residue selected from
(1) the residue of an anthraquinone dye having the formula

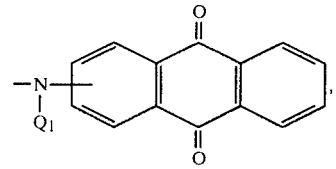

wherein,
$Q_1$ represents hydrogen, lower alkyl or lower hydroxy alkyl, the aromatic rings of said residue optionally having at least one substituent selected from amino, amino substituted by 1-2 lower alkyl groups, hydroxy, sulfonamide, amide, halogen, nitro, sulfonate or carboxylate,
(2) the residue of a nitro dye having the formula

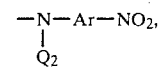

wherein
$Q_2$ represents hydrogen, lower alkyl or lower hydroxy alkyl,
Ar represents an aromatic group selected phenyl or phenyl substituted by amino, substituted amino, lower alkyloxy or hydroxy,
(3) the residue of a molecule of an azo dye having the formula,

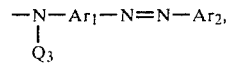

wherein
$Q_3$ represents hydrogen, lower alkyl or hydroxyalkyl,
$Ar_1$ and $Ar_2$, each independently represent an aromatic group selected from a benzenic, naphthalenic, indazolic, benzimidazolic, thiazolic, imidazolic, quinoleinic, pyridinic or thiazolic group,
(4) the residue of an azinic dye selected from an oxazinic or thiazinic group, and
(5) the residue of a triphenylmethane dye.

12. A process for preparing the dye polymer of claim 1 comprising reacting polydehydroaspartic acid of the formula

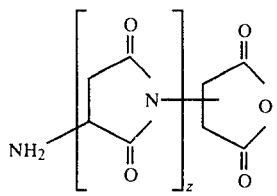 (V)

wherein z is a whole number ranging from 15 to 500, with at least one amine of the formula, R—NH—$(CH_2)_x$—X, wherein x, R and X have the meanings given in claim 1, at a rate of $m_1$ moles of said amine per mole of said polydehydroaspartic acid, $m_1$ being a whole or decimal number ranging from 1 to $z+1$ and being greater than $z+1$ when an excess of said amine is used.

13. The process of claim 12 wherein when $m_1$ is lower than z, the resulting product is further reacted with
(1) at least one further amine selected from an amine of the formula R′—NH—R″ or an amine of the formula R′″—NH—$(CH_2)_y$—Y, or both, wherein
R′ represents hydrogen, lower hydroxyalkyl, alkyl having 1–18 carbon atoms or alkenyl having 2–18 carbon atoms,
R″ represents hydrogen, lower hydroxyalkyl or lower alkyl, or R′ and R″ together with the nitrogen atom to which they are attached form a 5 or 6 chain ring, said ring optionally containing another heteroatom selected from oxygen and nitrogen,
R′″ represents hydrogen or lower alkyl,
y represents a whole number ranging from 2 to 6 and Y represents

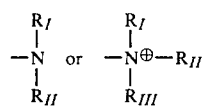

$Z^{\ominus}$ wherein
$R_I$, $R_{II}$ and $R_{III}$ each independently represent hydrogen, alkyl having up to 18 carbon atoms or alkenyl having up to 18 carbon atoms, or $R_I$ and $R_{II}$ together with the nitrogen atom to which they are attached form a 5 or 6 chain ring, said ring optionally containing another heteroatom selected from nitrogen or oxygen, and $Z^{\ominus}$ is an anion, or
(2) an alkali or alkaline earth base, or
(3) both (1) and (2).

14. A dye composition comprising in an appropriate vehicle from 0.005 to 15 weight percent based on the total weight of said composition of at least one dye polymer of claim 1.

15. The composition of claim 14 wherein said dye polymer is present in an amount ranging from 0.02 to 8 weight percent of said composition.

16. The composition of claim 14 wherein said vehicle comprises water and said composition is provided in the form of a composition ready for use, a concentrate, an after shampoo lotion, a dye shampoo, or a dye hair setting lotion.

17. The composition of claim 14 wherein said vehicle comprises water and said composition also includes, in addition to said dye polymer, another hair setting lotion film forming polymer.

18. The composition of claim 16 which also includes an effective amount of a non-polymer dye.

19. The composition of claim 16 which also includes an effective amount of an oxidation dye.

20. A two-part dye composition, said two parts to be admixed at the time of use and being packaged in an appropriate container, said first part comprising the composition of claim 19 and said second part comprising an oxidizing agent in an amount sufficient to transform by oxidative condensation the oxidation dyes of said first part into colored compounds.

21. A process for dyeing keratinic fibers comprising applying to said fibers for a time sufficient to obtain the color desired, an effective amount of the dye composition defined in claim 14.

* * * * *